(12) United States Patent
Dacquay et al.

(10) Patent No.: US 7,862,540 B2
(45) Date of Patent: Jan. 4, 2011

(54) OPHTHALMIC INJECTION DEVICE USING SHAPE MEMORY ALLOY

(75) Inventors: Bruno Dacquay, Irvine, CA (US); Casey Lind, Irvine, CA (US); Mike Martin, Newport Beach, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 824 days.

(21) Appl. No.: 11/752,064

(22) Filed: May 22, 2007

(65) Prior Publication Data
US 2007/0270777 A1 Nov. 22, 2007

Related U.S. Application Data

(63) Continuation-in-part of application No. 11/435,906, filed on May 17, 2006, now abandoned.

(60) Provisional application No. 60/921,497, filed on Oct. 16, 2006, provisional application No. 60/921,498, filed on Oct. 16, 2006, provisional application No. 60/921,499, filed on Oct. 16, 2006.

(51) Int. Cl.
*A61M 31/00* (2006.01)
(52) U.S. Cl. ............ 604/95.05; 604/530; 604/531
(58) Field of Classification Search ............ 604/521, 604/890.1, 95.01, 95.03, 530–531, 294, 298, 604/95.05; 606/28
See application file for complete search history.

(56) References Cited

U.S. PATENT DOCUMENTS

| 1,252,614 | A | 1/1918 | Pieper et al. |
|---|---|---|---|
| 3,089,815 | A | 5/1963 | Lieb et al. |
| 3,608,549 | A | 9/1971 | Merrill |
| 3,892,537 | A | 7/1975 | Gulati et al. |
| 3,982,537 | A | 9/1976 | Bucalo |
| 4,007,742 | A | 2/1977 | Banko |
| 4,030,499 | A | 6/1977 | Bucalo |

(Continued)

FOREIGN PATENT DOCUMENTS

EP 0348146 A1 12/1989

(Continued)

OTHER PUBLICATIONS

U.S. Appl. No. 11/200,452, filed Aug. 9, 2005, Hopkins.

(Continued)

*Primary Examiner*—Kevin C Sirmons
*Assistant Examiner*—Deanna K Hall
(74) *Attorney, Agent, or Firm*—Kenneth D. Bassinger

(57) ABSTRACT

An ophthalmic injection device has a dispensing chamber housing, a needle fluidly coupled to a dispensing chamber, a power source for providing current to the dispensing chamber housing, a controller for controlling the power source, and a housing at least partially enclosing the dispensing chamber housing, the power source, and the controller. The dispensing chamber housing is made of a shape memory alloy and has an inner surface defining a dispensing chamber for receiving a quantity of a substance. The controller directs a first current to the dispensing chamber housing to heat the substance contained in the dispensing chamber and a second current to the dispensing chamber housing to alter the shape of the dispensing chamber housing to deliver the substance.

10 Claims, 7 Drawing Sheets

U.S. PATENT DOCUMENTS

| | | | |
|---|---|---|---|
| 4,054,138 A | 10/1977 | Bucalo | |
| 4,122,850 A | 10/1978 | Bucalo | |
| 4,184,510 A | 1/1980 | Murry et al. | |
| 4,246,932 A | 1/1981 | Raines | |
| 4,265,618 A | 5/1981 | Herskovitz et al. | |
| 4,357,136 A | 11/1982 | Herskovitz et al. | |
| 4,392,827 A | 7/1983 | Martin | |
| 4,474,752 A | 10/1984 | Haslam et al. | |
| 4,484,915 A | 11/1984 | Tartaglia | |
| 4,582,488 A | 4/1986 | Newman | |
| 4,684,344 A | 8/1987 | Brockway et al. | |
| 4,704,088 A | 11/1987 | Newman | |
| 4,713,446 A | 12/1987 | DeVore et al. | |
| 4,795,423 A | 1/1989 | Osterholm | |
| 4,830,855 A | 5/1989 | Stewart | |
| 4,992,045 A | 2/1991 | Beisel | |
| 5,066,276 A | 11/1991 | Wang | |
| 5,120,307 A | 6/1992 | Wang | |
| 5,328,481 A | 7/1994 | Wang | |
| 5,336,175 A | 8/1994 | Mames | |
| 5,360,413 A | 11/1994 | Leason et al. | |
| 5,370,630 A | 12/1994 | Smidebush et al. | |
| 5,476,511 A | 12/1995 | Gwon et al. | |
| 5,487,725 A | 1/1996 | Peyman | |
| 5,582,595 A | 12/1996 | Haber et al. | |
| 5,620,700 A | 4/1997 | Berggren et al. | |
| 5,743,886 A | 4/1998 | Lynn et al. | |
| 5,773,019 A | 6/1998 | Ashton et al. | |
| 5,783,205 A | 7/1998 | Berggren et al. | |
| 5,824,072 A | 10/1998 | Wong | |
| 5,860,949 A | 1/1999 | Chen | |
| 5,928,663 A | 7/1999 | Peyman | |
| 5,984,889 A | 11/1999 | Christ et al. | |
| 6,210,357 B1 | 4/2001 | Morris | |
| 6,270,343 B1 | 8/2001 | Martin | |
| 6,290,690 B1 | 9/2001 | Huculak et al. | |
| 6,364,865 B1 | 4/2002 | Lavi et al. | |
| 6,372,245 B1 | 4/2002 | Bowman et al. | |
| 6,413,245 B1 | 7/2002 | Yaacobi et al. | |
| 6,419,656 B1 | 7/2002 | Vetter et al. | |
| 6,436,143 B1 | 8/2002 | Ross et al. | |
| 6,488,659 B1 | 12/2002 | Rosenman | |
| 6,520,930 B2 | 2/2003 | Critchlow et al. | |
| 6,585,700 B1 | 7/2003 | Trocki et al. | |
| 6,595,979 B1 | 7/2003 | Epstein et al. | |
| 6,635,267 B1 | 10/2003 | Miyoshi et al. | |
| 6,645,179 B1 | 11/2003 | Ishikawa et al. | |
| 6,726,654 B2 | 4/2004 | Rosenman | |
| 6,940,209 B2 | 9/2005 | Henderson | |
| 6,981,499 B2 * | 1/2006 | Anderson et al. | 128/200.23 |
| 6,991,457 B2 | 1/2006 | Kazen et al. | |
| 7,176,030 B2 | 2/2007 | Faries, Jr. et al. | |
| 2002/0055720 A1 | 5/2002 | Hohlfelder et al. | |
| 2003/0055380 A1 | 3/2003 | Flaherty | |
| 2003/0125665 A1 | 7/2003 | Rosenman | |
| 2004/0039253 A1 | 2/2004 | Peyman et al. | |
| 2004/0052761 A1 | 3/2004 | Vernon et al. | |
| 2004/0133155 A1 | 7/2004 | Varner et al. | |
| 2004/0176720 A1 | 9/2004 | Kipfer | |
| 2004/0210200 A1 | 10/2004 | Gerondale et al. | |
| 2004/0231667 A1 | 11/2004 | Horton et al. | |
| 2005/0065477 A1 | 3/2005 | Jost | |
| 2005/0177137 A1 | 8/2005 | Kipfer | |
| 2006/0047250 A1 | 3/2006 | Hickingbotham | |

FOREIGN PATENT DOCUMENTS

| | | |
|---|---|---|
| EP | 0398394 | 11/1990 |
| GB | 1551767 | 8/1979 |
| WO | WO 82/03761 A1 | 11/1982 |
| WO | WO 87/00029 A1 | 1/1987 |
| WO | WO 96/03978 A1 | 2/1996 |
| WO | WO 99/33853 A2 | 7/1999 |
| WO | WO 01/10482 A1 | 2/2001 |
| WO | WO 2006/050008 A1 | 5/2006 |

OTHER PUBLICATIONS

U.S. Appl. No. 11/435,906, filed May 17, 2005, Dacquay et al.
U.S. Appl. No. 11/486,870, filed Jul. 14, 2006, Marsh et al.
"Ultra™ 2800 Positive Displacement Dispenser"; 2004; EFD, Inc. Brochure XP 1104 vol. 11.10; 2 pages.
"Parker: Your Resource For Motion And Fluid Control Components, Systems and Solutions—System Solutions For Life Sciences"; 2003; Aurora Instruments, LLC Brochure; 8 pages.

* cited by examiner

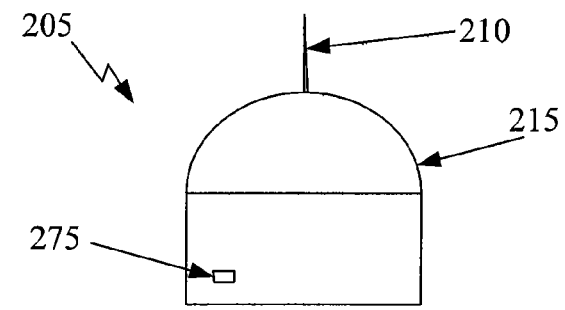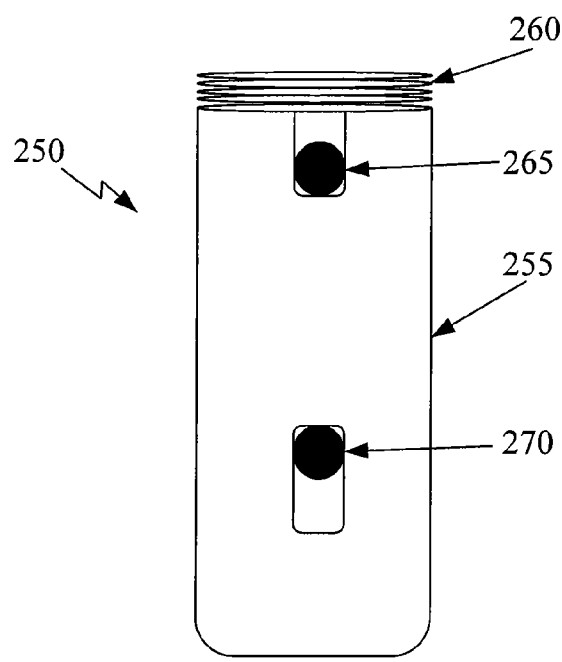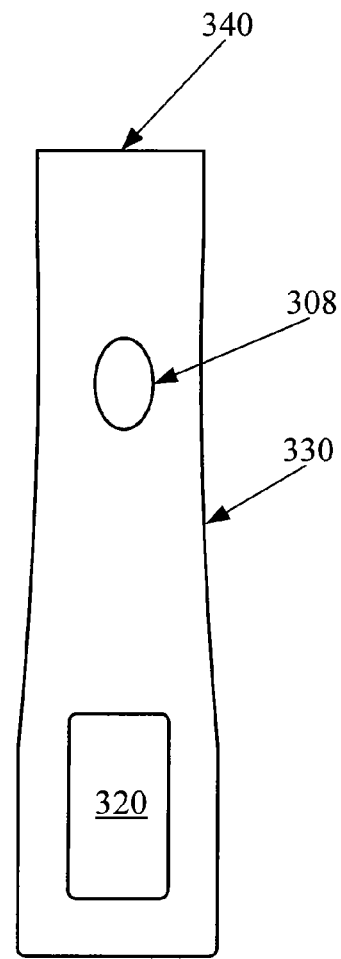
Fig. 2
Fig. 3

OPHTHALMIC INJECTION DEVICE USING SHAPE MEMORY ALLOY

RELATED APPLICATIONS

This application is a non-provisional of U.S. Patent Application No. 60/921,497 filed Oct. 16, 2006, U.S. Patent Application No. 60/921,498 filed Oct. 16, 2006, U.S. Patent Application No. 60/921,499 filed Oct. 16, 2006, and is a continuation-in-part of U.S. patent application Ser. No. 11/435,906 filed May 17, 2006, now abandoned.

BACKGROUND OF THE INVENTION

The present invention relates to a medical device and more particularly to an ophthalmic drug delivery device using a shape memory alloy.

Several diseases and conditions of the posterior segment of the eye threaten vision. Age related macular degeneration (ARMD), choroidal neovascularization (CNV), retinopathies (e.g., diabetic retinopathy, vitreoretinopathy), retinitis (e.g., cytomegalovirus (CMV) retinitis), uveitis, macular edema, glaucoma, and neuropathies are several examples.

These, and other diseases, can be treated by injecting a drug into the eye. Such injections are typically manually made using a conventional syringe and needle. FIG. 1 is a perspective view of a prior art syringe used to inject drugs into the eye. In FIG. 1, the syringe includes a needle 105, a luer hub 110, a chamber 115, a plunger 120, a plunger shaft 125, and a thumb rest 130. As is commonly known, the drug to be injected is located in chamber 115. Pushing on the thumb rest 130 causes the plunger 120 to expel the drug through needle 105.

In using such a syringe, the surgeon is required to puncture the eye tissue with the needle, hold the syringe steady, and actuate the syringe plunger (with or without the help of a nurse) to inject the fluid into the eye. The volume injected is typically not controlled in an accurate manner because the vernier on the syringe is not precise relative to the small injection volume. Fluid flow rates are uncontrolled. Reading the vernier is also subject to parallax error. Tissue damage may occur due to an "unsteady" injection. Reflux of the drug may also occur when the needle is removed from the eye.

An effort has been made to control the delivery of small amounts of liquids. A commercially available fluid dispenser is the ULTRA™ positive displacement dispenser available from EFD Inc. of Providence, R.I. The ULTRA dispenser is typically used in the dispensing of small volumes of industrial adhesives. It utilizes a conventional syringe and a custom dispensing tip. The syringe plunger is actuated using an electrical stepper motor and an actuating fluid. Parker Hannifin Corporation of Cleveland, Ohio distributes a small volume liquid dispenser for drug discovery applications made by Aurora Instruments LLC of San Diego, Calif. The Parker/Aurora dispenser utilizes a piezo-electric dispensing mechanism. Ypsomed, Inc. of Switzerland produces a line of injection pens and automated injectors primarily for the self-injection of insulin or hormones by a patient. This product line includes simple disposable pens and electronically-controlled motorized injectors.

U.S. Pat. No. 6,290,690 discloses an ophthalmic system for injecting a viscous fluid (e.g. silicone oil) into the eye while simultaneously aspirating a second viscous fluid (e.g. perflourocarbon liquid) from the eye in a fluid/fluid exchange during surgery to repair a retinal detachment or tear. The system includes a conventional syringe with a plunger. One end of the syringe is fluidly coupled to a source of pneumatic pressure that provides a constant pneumatic pressure to actuate the plunger. The other end of the syringe is fluidly coupled to an infusion cannula via tubing to deliver the viscous fluid to be injected.

It would be desirable to have a portable hand piece for injecting a drug into the eye that includes reliable technology using few parts. Shape memory alloy provides a technology that can be adapted for such use. The hand piece may be a single piece unit or a two-piece device. Placing the more expensive components, including electronics and a drive mechanism, in a reusable assembly, while keeping the sterile components in a disposable assembly, improves the efficiency and cost-effectiveness of a drug delivery system. However, a single piece device with a relatively simple structure is also feasible. Such a system provides numerous benefits over prior art injectors.

SUMMARY OF THE INVENTION

In one embodiment consistent with the principles of the present invention, the present invention is an ophthalmic injection system having a tip segment and a limited reuse assembly. The tip segment includes a dispensing chamber housing, a needle fluidly coupled to a dispensing chamber, and a first housing at least partially enclosing the dispensing chamber housing. The dispensing chamber housing is made of a shape memory alloy. The inner surface defines a dispensing chamber for receiving a quantity of a substance. The limited reuse assembly includes a power source for providing current to the dispensing chamber housing, a controller for controlling the power source, and a second housing at least partially enclosing the power source and the controller. The controller directs a first current to the dispensing chamber housing to heat the substance contained in the dispensing chamber and a second current to the dispensing chamber housing to alter the shape of the dispensing chamber housing to deliver the substance.

In another embodiment consistent with the principles of the present invention, the present invention is an ophthalmic injection device having a dispensing chamber housing, a needle fluidly coupled to a dispensing chamber, a power source for providing current to the dispensing chamber housing, a controller for controlling the power source, and a housing at least partially enclosing the dispensing chamber housing, the power source, and the controller. The dispensing chamber housing is made of a shape memory alloy and has an inner surface defining a dispensing chamber for receiving a quantity of a substance. The controller directs a first current to the dispensing chamber housing to heat the substance contained in the dispensing chamber and a second current to the dispensing chamber housing to alter the shape of the dispensing chamber housing to deliver the substance.

In another embodiment consistent with the principles of the present invention, the present invention is a method of delivering a substance into an eye including receiving a first input indicating that a substance is to be heated, in response to the first input, sending a first current to a dispensing chamber housing made of a shape memory alloy to heat the substance contained therein, receiving a second input indicating that the substance is to be delivered, and sending a second current to the dispensing chamber housing to deliver the substance.

It is to be understood that both the foregoing general description and the following detailed description are exemplary and explanatory only and are intended to provide further explanation of the invention as claimed. The following description, as well as the practice of the invention, set forth and suggest additional advantages and purposes of the invention.

BRIEF DESCRIPTION OF THE DRAWINGS

The accompanying drawings, which are incorporated in and constitute a part of this specification, illustrate several embodiments of the invention and together with the description, serve to explain the principles of the invention.

FIG. 2 is one view of an ophthalmic medical device including a disposable tip segment and a limited reuse assembly according to an embodiment of the present invention.

FIG. 3 is another embodiment of a limited reuse assembly according to the principles of the present invention.

DETAILED DESCRIPTION OF THE PREFERRED EMBODIMENTS

Figure 1:
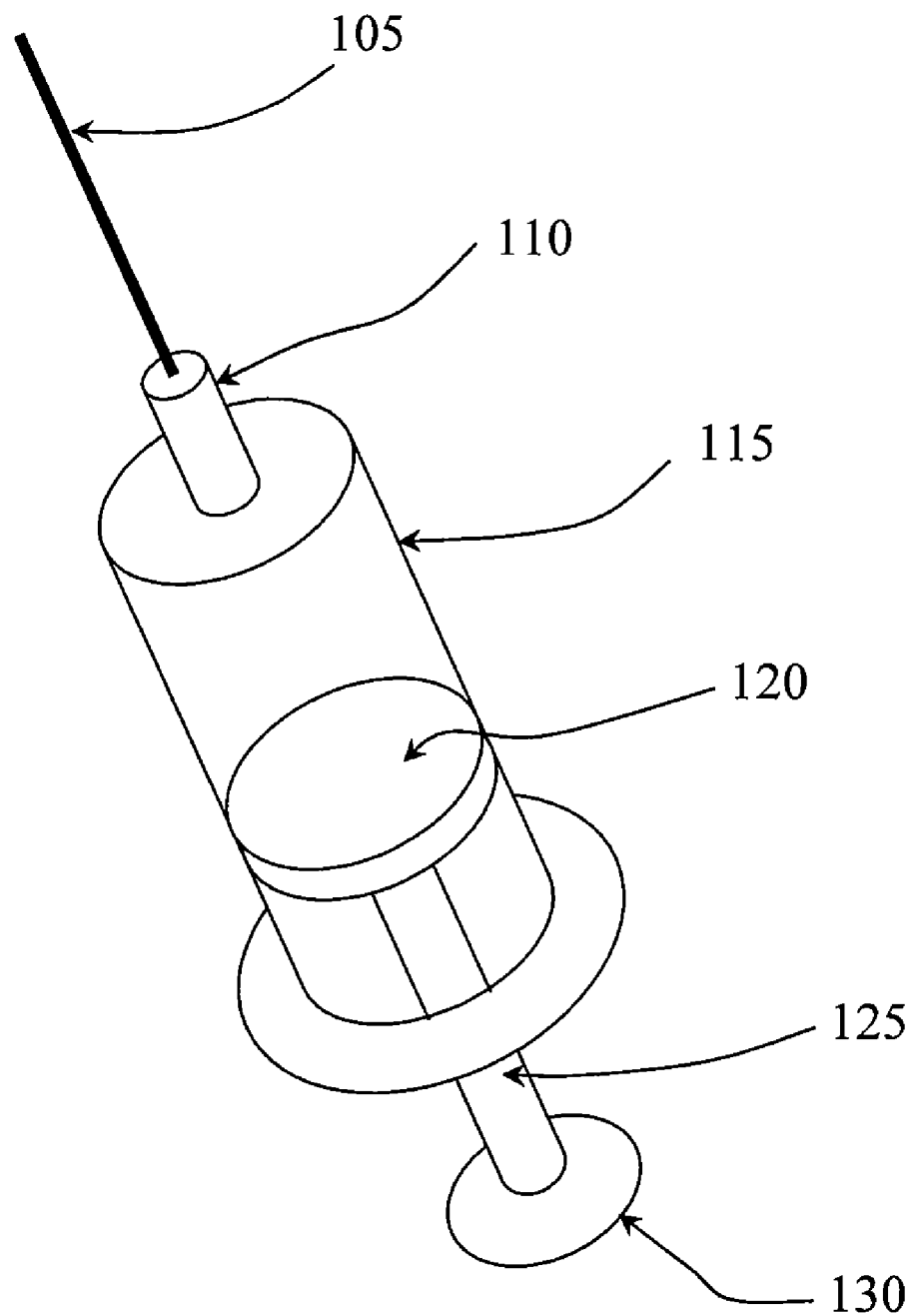
FIG. 1 is a perspective view of a prior art syringe.

Reference is now made in detail to the exemplary embodiments of the invention, examples of which are illustrated in the accompanying drawings. Wherever possible, the same reference numbers are used throughout the drawings to refer to the same or like parts.

FIG. 2 is one view of an ophthalmic medical device including a disposable tip segment and a limited reuse assembly according to an embodiment of the present invention. In FIG. 2, the medical device includes a tip segment 205 and a limited reuse assembly 250. The tip segment 205 includes a needle 210, a housing 215, and an optional light 275. The limited reuse assembly 250 includes a housing 255, a switch 270, a lock mechanism 265, and a threaded portion 260.

Tip segment 205 is capable of being connected to and removed from limited reuse assembly 250. In this embodiment, tip segment 205 has a threaded portion on an interior surface of housing 215 that screws onto the threaded portion 260 of limited reuse assembly 250. In addition, lock mechanism 265 secures tip segment 215 to limited reuse assembly 250. Lock mechanism 265 may be in the form of a button, a sliding switch, or a cantilevered mechanism. Other mechanisms for connecting tip segment 205 to limited reuse assembly 250, such as those involving structural features that mate with each other, are commonly known in the art and are within the scope of the present invention.

Needle 210 is adapted to deliver a substance, such as a drug, into an eye. Needle 210 may be of any commonly known configuration. Preferably, needle 210 is designed such that its thermal characteristics are conducive to the particular drug delivery application. For example, when a heated drug is to be delivered, needle 210 may be relatively short (several millimeters) in length to facilitate proper delivery of the drug.

Switch 270 is adapted to provide an input to the system. For example, switch 270 may be used to activate the system or to turn on a heater. Other switches, buttons, or user-directed control inputs are commonly known and may be employed with limited reuse assembly 250 and/or tip segment 205.

Optional light 275 is illuminated when tip segment 205 is ready to be used. Optional light 275 may protrude from housing 215, or it may be contained within housing 215, in which case, optional light 275 may be seen through a clear portion of housing 215. In other embodiments, optional light 275 may be replaced by an indicator, such as a liquid crystal display, segmented display, or other device that indicates a status or condition of disposable tip segment 205. For example, optional light 275 may also pulse on and off to indicate other states, such as, but not limited to a system error, fully charged battery, insufficiently charged battery or faulty connection between the tip segment 205 and limited use assembly 250. While shown on tip segment 205, optional light 275 or other indicator may be located on limited reuse assembly 250.

FIG. 3 is another embodiment of a limited reuse assembly according to the principles of the present invention. Limited reuse assembly 250 includes a button 308, a display 320, and a housing 330. Disposable tip segment 205 attaches to end 340 of limited reuse assembly 250. Button 308 is actuated to provide an input to the system. As with switch 270, button 308 may activate a heater or other temperature control device or initiate actuation of a plunger. Display 320 is a liquid crystal display, segmented display, or other device that indicates a status or condition of disposable tip segment 205 or limited reuse assembly 250.

Figure 4:
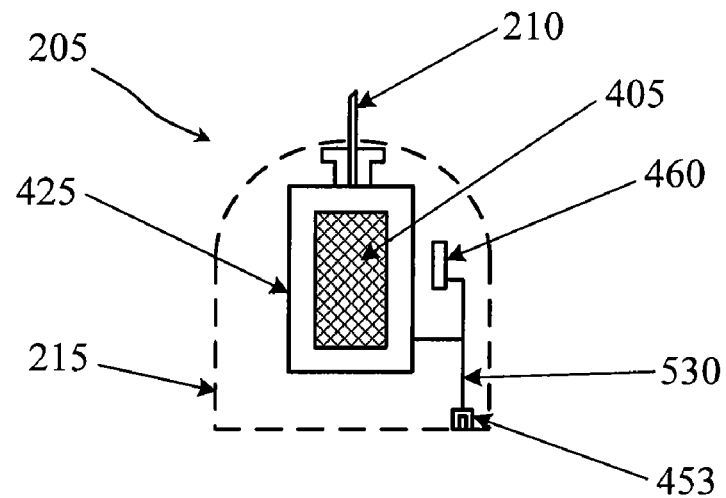
FIG. 4 is cross section view of a disposable tip segment and a limited reuse assembly according to an embodiment of the present invention.
Figure 4:
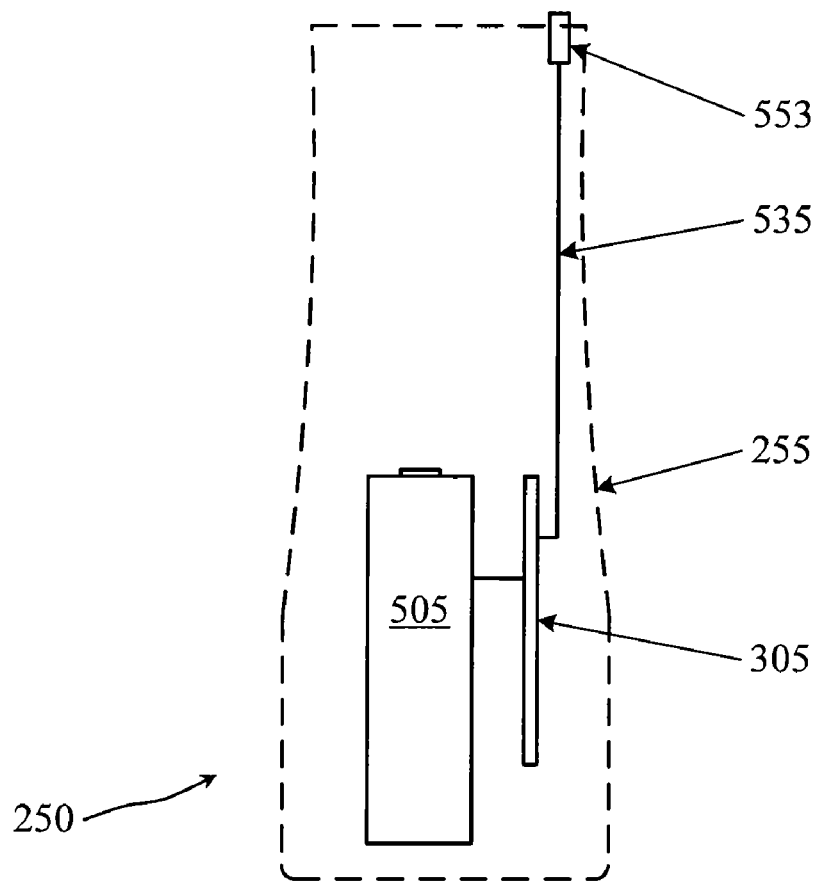

FIG. 4 is cross section view of a disposable tip segment and a limited reuse assembly according to an embodiment of the present invention. FIG. 4 shows how tip segment 205 interfaces with limited reuse assembly 250. In the embodiment of FIG. 4, tip segment 205 includes dispensing chamber housing 425, tip segment housing 215, thermal sensor 460, needle 210, dispensing chamber 405, interface 530, and tip interface connector 453. Limited reuse assembly 250 includes power source 505, controller 305, limited reuse assembly housing 255, interface 535, and limited reuse assembly interface connector 553.

In FIG. 4, dispensing chamber housing 425 is tubular or cylindrical in shape and is made of a shape memory alloy ("SMA"). Shape memory alloys, such as various Nitinol (a nickel-titanium alloy) alloys, hold a deformed shape at room temperature. When heated to a higher temperature, the SMA reverts to its non-deformed shape. In other words, a shape memory alloy (also known as a smart alloy or memory metal) is a metal that "remembers" its geometry. After an SMA has been deformed from its original atomic configuration, it regains its original geometry by itself during heating. These properties are due to a temperature-dependent martensitic phase transformation from a low-symmetry to a highly symmetric crystallographic structure. Those crystal structures are known as martensite and austenite. The three main types of SMA are copper-zinc-aluminum, copper-aluminum-nickel, and nickel-titanium (Ni—Ti) alloys. The temperatures at which the SMA changes its crystallographic structure are characteristic of the alloy, and can be tuned by varying the elemental ratios.

For a dispensing chamber housing 425 made out of Nitinol, the Nitinol is in a deformed shape at room temperature. In this deformed shape, the Nitinol has a martensitic crystal structure. In this deformed shape, dispensing chamber 405 has a higher volume and can hold a substance. When a current is passed through dispensing chamber housing 425, its temperature rises. When the temperature of the Nitinol dispensing chamber housing 425 reaches 60 or 70 degrees Celsius, the Nitinol will revert to its non-deformed shape. In this process, the Nitinol changes from a martensitic crystal structure to an austenic crystal structure. In this non-deformed shape, dispensing chamber 405 has a lower volume than in the deformed shape. Therefore, a current can be passed through dispensing chamber housing 425 to initially heat a substance in it, and then to change the shape of dispensing chamber 405 to expel that substance.

Needle 210 is fluidly coupled to dispensing chamber 405. As such, a substance contained in dispensing chamber 405 can pass through needle 210 and into an eye. Interface 530 connects dispensing chamber housing 425 with tip interface connector 453.

Optional thermal sensor 460 provides temperature information to assist in controlling the operation of dispensing chamber housing 425. Thermal sensor 460 may be located near dispensing chamber housing 425 and measure a temperature near dispensing chamber housing 425 or may be located in thermal contact with dispensing chamber housing 425, in which case it measures a temperature of dispensing chamber housing 425. Thermal sensor 460 may be any of a number of different devices that can provide temperature information. For example, thermal sensor 460 may be a thermocouple or a resistive device whose resistance varies with temperature. Thermal sensor is also electrically coupled to interface 530 or other similar interface.

In limited reuse assembly 250, power source 505 is typically a rechargeable battery, such as a lithium ion battery, although other types of batteries may be employed. In addition, any other type of power cell is appropriate for power source 505. Power source 505 provides current to dispensing chamber housing 425 to heat it and change its shape. Optionally, power source 505 can be removed from housing 255 through a door or other similar feature (not shown).

Controller 305 is typically an integrated circuit with power, input, and output pins capable of performing logic functions. In various embodiments, controller 305 is a targeted device controller. In such a case, controller 305 performs specific control functions targeted to a specific device or component, such as a temperature control device or a power supply. For example, a temperature control device controller has the basic functionality to control current delivered to dispensing chamber housing 425. In other embodiments, controller 305 is a microprocessor. In such a case, controller 305 is programmable so that it can function to control more than one component of the device. In other cases, controller 305 is not a programmable microprocessor, but instead is a special purpose controller configured to control different components that perform different functions. While depicted as one component in FIG. 4, controller 305 may be made of many different components or integrated circuits.

Controller 305 is connected via interface 535 to limited reuse assembly interface connector 553. Limited reuse assembly interface connector 553 is located on a top surface of limited reuse assembly housing 255. In this manner, limited reuse assembly interface connector 553 is adapted to be connected with tip interface connector 453 to provide an electrical connection between tip segment 205 and limited reuse assembly 250.

An interface between power source 505 and controller 305 allows controller 305 to control operation of power source 505. In such a case, controller 305 may control the charging and the discharging of power source 505 when power source 505 is a rechargeable battery.

In operation, when tip segment 205 is connected to limited reuse assembly 250, controller 305 controls the operation of dispensing chamber housing 425. Controller 305 directs current from power source 505 to dispensing chamber housing 425. When dispensing chamber housing 425 is made of Nitinol, a first current is sent to it to increase its temperature and heat a substance contained in dispensing chamber 405. A second, higher current is subsequently sent to dispensing chamber housing 425 to cause it to change its shape and expel the substance through needle 210.

A substance to be delivered into an eye, typically a drug suspended in a phase transition compound, is located in dispensing chamber 405. In this manner, the drug and phase transition compound are contacted by the inner surface of dispensing chamber housing 425. The phase transition compound is in a solid or semi-solid state at lower temperatures and in a more liquid state at higher temperatures. Such a compound can be heated by the application of current to dispensing chamber housing 425 to a more liquid state and injected into the eye where it forms a bolus that erodes over time.

In one embodiment of the present invention, the substance located in dispensing chamber 405 is a drug that is preloaded into the dispensing chamber. In such a case, tip segment 205 is appropriate as a single use consumable product. Such a disposable product can be assembled at a factory with a dosage of a drug installed.

Figure 5A:
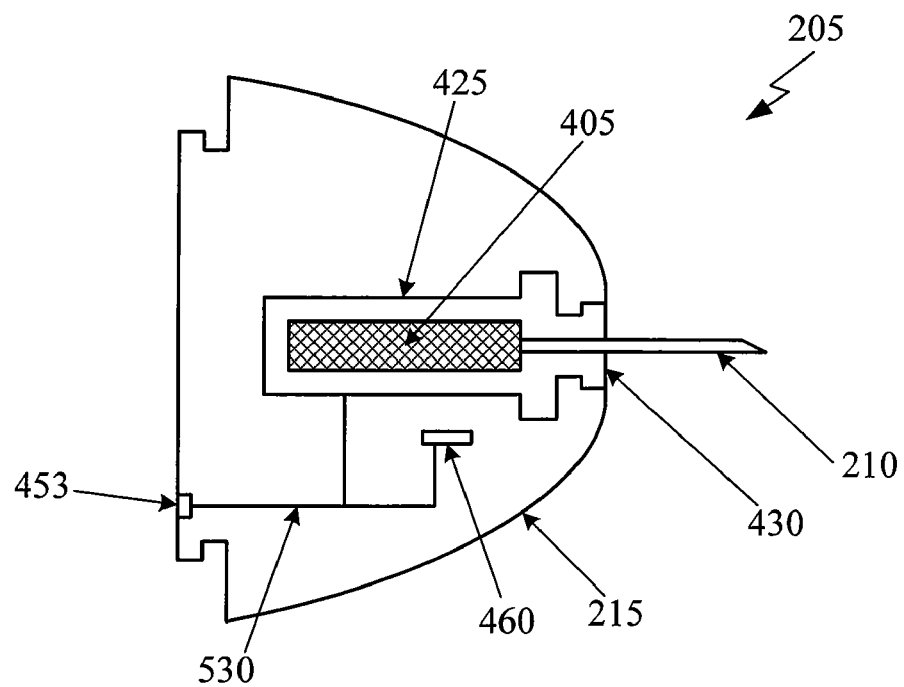
FIGS. 5A and 5B are exploded cross section views of disposable tip segments for an ophthalmic medical device according to an embodiment of the present invention.
Figure 5B:
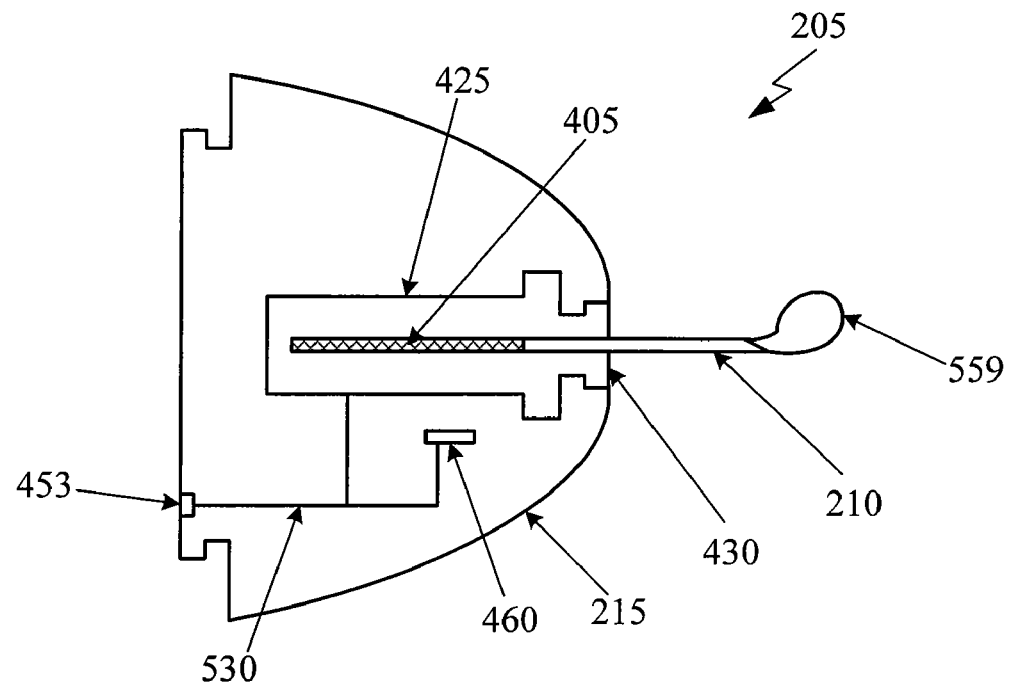

FIGS. 5A and 5B are exploded cross section views of disposable tip segments for an ophthalmic medical device according to an embodiment of the present invention. In FIG. 5A, dispensing chamber housing 425 is in its deformed shape (its crystalline structure is martenistic). In FIG. 5B, dispensing chamber housing is in its non-deformed shape (its crystalline structure is austenic). In FIGS. 5A and 5B, an optional luer is also picture to secure needle 210.

In FIG. 5A, a first current is applied to dispensing chamber housing 425. This first current is less than that required to heat dispensing chamber housing 425 to a point at which it changes shape. However, this first current heats dispensing chamber housing 425 to a temperature above room temperature but below the temperature at which it changes shape. In this manner, a substance located in dispensing chamber 425 is heated because it is in thermal contact with the interior surface of dispensing chamber housing 425.

For example, when dispensing chamber housing is made of Nitinol, a first current may raise the temperature of dispensing chamber housing 425 to 50 degrees Celsius. At this temperature, a phase transition compound located in dispensing chamber housing can be "melted" to a more liquid state or to a viscosity suitable for injection into an eye. However, at this point, the dispensing chamber housing maintains its deformed shape (and the dispensing chamber 405 has a higher volume).

A second current can be applied to raise the temperature of dispensing chamber housing 425 (made of Nitinol) to above 60 or 70 degrees Celsius. At this temperature, dispensing chamber housing 425 changes shape as depicted in FIG. 5B. The volume of dispensing chamber 405 is reduced, thus expelling a substance 559 that was contained in dispensing chamber 405. In other words, after the phase transition compound located in dispensing chamber 405 is heated, the second current causes the volume of dispensing chamber 405 to decrease and expel the phase transition compound through needle 210 and into an eye.

The first current applied to the dispensing chamber housing 425 can be regulated to control the temperature of the substance contained in dispensing chamber 405. For example, the amount of current (typically DC current) can be controlled to precisely control the temperature of dispensing chamber housing 425. The more current applied to dispensing chamber housing 425, the greater its temperature. Thermal sensor 460 provides temperature information to controller 305, so that it can control the amount of current sent to dispensing chamber housing 425. Controller 305 may employ any of a number of different control algorithms, such as, for example, a PID algorithm.

Likewise, the second current applied to dispensing chamber housing 425 can be regulated to control a dosage and rate of delivery of the substance in dispensing chamber 405. A shape metal alloy, such as Nitinol, may transform its shape gradually over a temperature range. For example, the shape of dispensing chamber 425 may change over a range of 5 or 10 degrees Celsius. The precise control of the current applied to dispensing chamber housing 425 results in the precise control of the temperature of dispensing chamber housing 425. In this manner, the transition of dispensing chamber housing 425 from a deformed state to a non-deformed state can be controlled. The control of the change in shape results in control of the rate of delivery of the substance.

Figure 6:
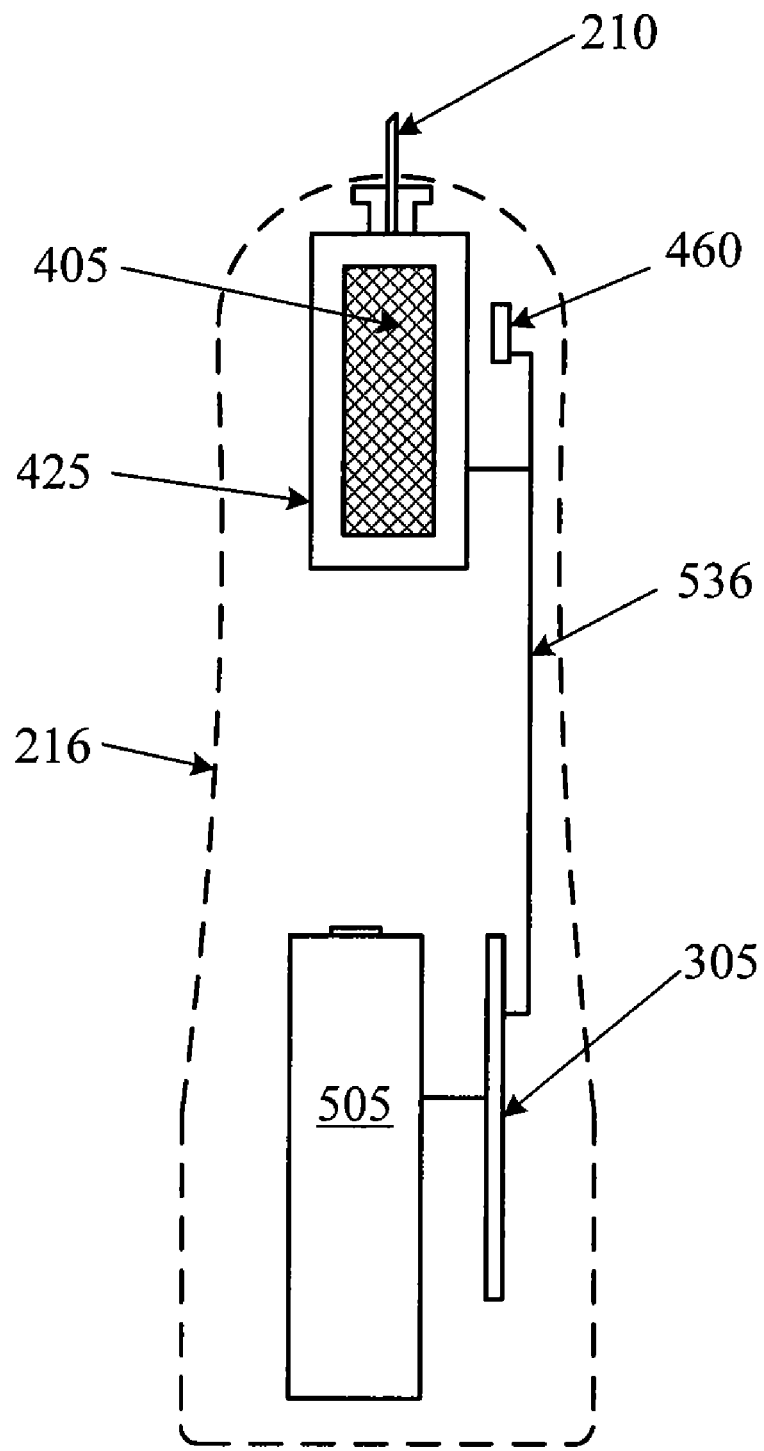
FIG. 6 is a cross section view of an ophthalmic injection device according to the principles of the present invention.

FIG. 6 is a cross section view of an ophthalmic injection device according to the principles of the present invention. In FIG. 6, the injection device is integrated into a single unit. The single piece device of FIG. 6 operates in the same manner as the two piece device previously described. In FIG. 6, the device includes dispensing chamber housing 425, dispensing chamber 405, needle 210, thermal sensor 460, interface 536, controller 305, power source 505, and housing 216. In FIG. 6, a single interface 536 is used instead of two separate interfaces (530 and 535) and two separate connectors (453 and 553). Housing 216 encloses the components pictured.

Figure 7:
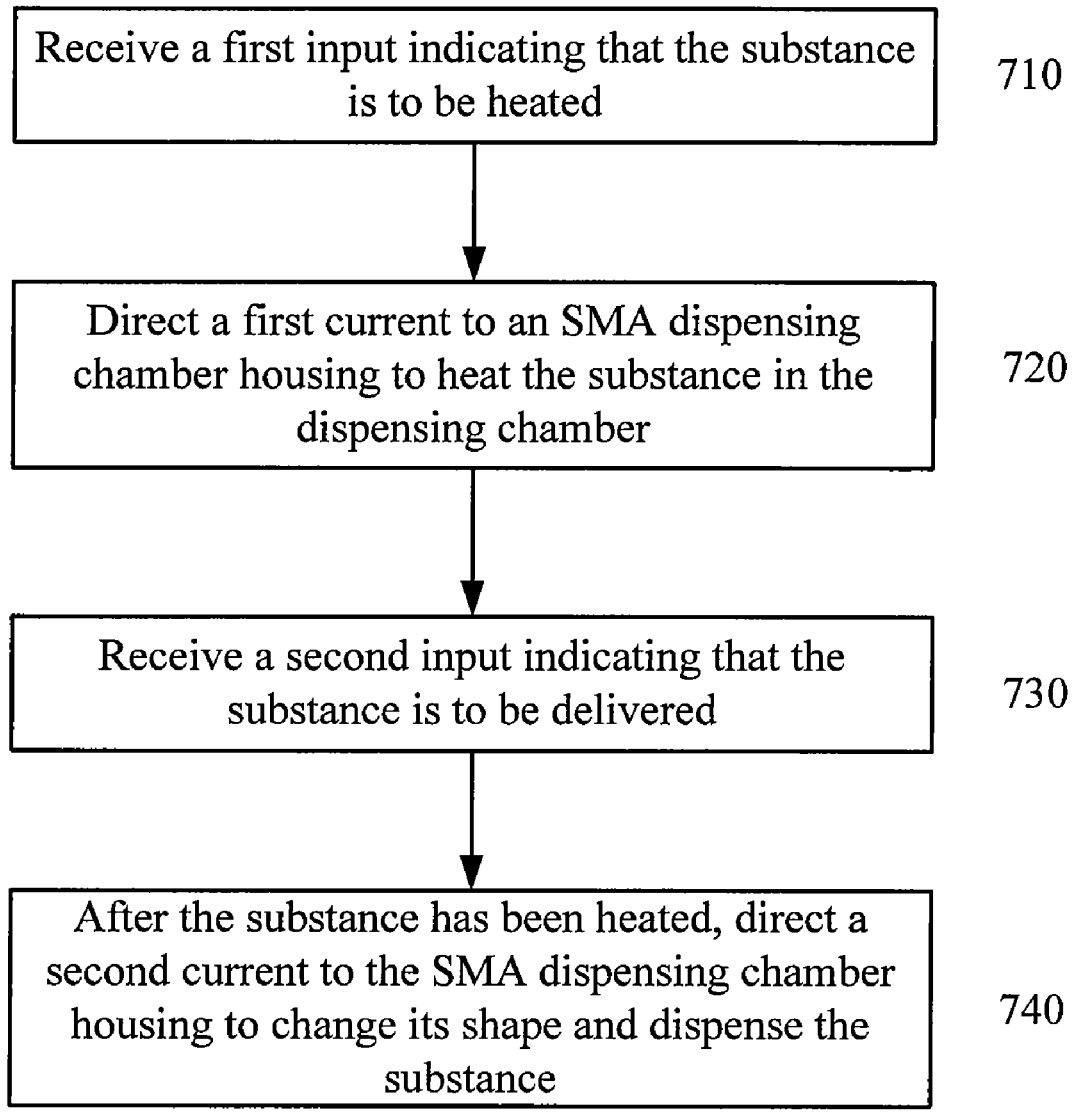
FIG. 7 is a flow chart of one method of delivering a substance into an eye using a shape memory alloy.

FIG. 7 is a method of delivering a substance into an eye using a shape memory alloy. In 710, a first input indicating that a substance is to be heated is received. In 720, a first current is directed to an SMA dispensing chamber housing to heat the substance in the dispensing chamber. In 730, a second input is received indicating that the substance is to be delivered. In 740, after the substance is heated, a second current is directed to the SMA dispensing chamber housing to change its shape and dispense the substance.

Figure 8:
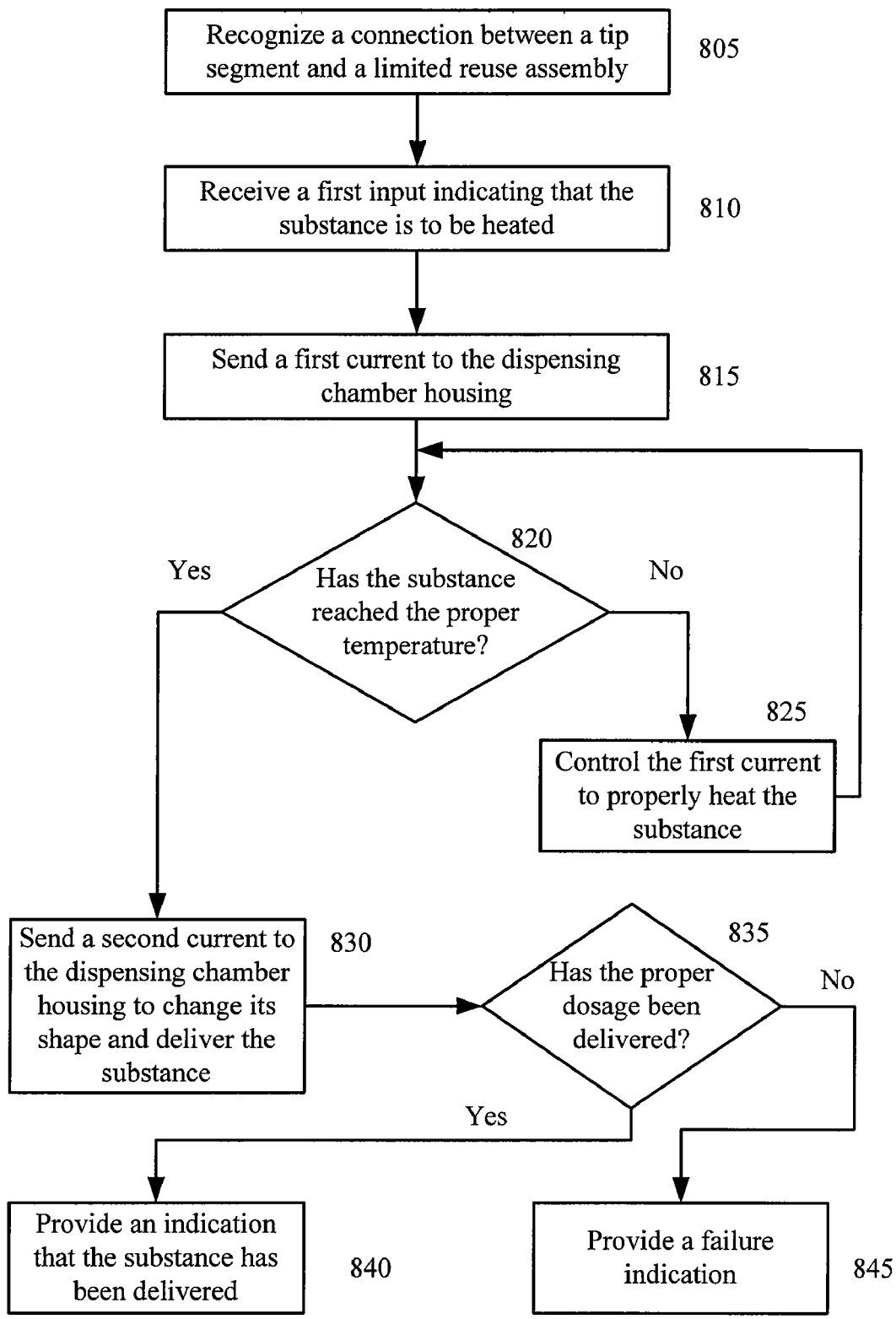
FIG. 8 is a flow chart of one method of delivering a substance into an eye using a shape memory alloy.

FIG. 8 is a method of delivering a substance into an eye using a shape memory alloy. In 805, a connection between a tip segment and a limited reuse assembly is recognized. In 810, a first input indicating that a substance is to be heated is received. In 815, a first current is sent to the dispensing chamber housing. In 820, a determination is made as to whether the substance has reached the proper temperature. If the substance has not reached the proper temperature, then in 825 the first current is controlled to properly heat the substance. If the substance has reached the proper temperature, then in 830, a second current is sent to the dispensing chamber housing to change its shape and deliver the substance. In 835, a determination is made as to whether the proper dosage has been delivered. If the proper dosage has been delivered, then in 840 an indication that the substance has been delivered is provided. If the proper dosage has not been delivered, then in 845 a failure indication is provided.

From the above, it may be appreciated that the present invention provides an improved system and methods for delivering precise volumes of a substance into an eye. The present invention provides a dispensing chamber housing made of a shape memory alloy that can heat and expel a substance. In one embodiment, a disposable tip segment that interfaces with a limited reuse assembly is employed. In another embodiment, a single unit is employed. The present invention is illustrated herein by example, and various modifications may be made by a person of ordinary skill in the art.

While the present invention is described in the context of a single-use drug delivery device, the present invention encompasses any injection device. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:

1. An ophthalmic injection device comprising:
  a dispensing chamber housing with a wall made of a shape memory alloy and having an inner surface and an outer surface, the inner surface defining a dispensing chamber for holding a quantity of a substance;
  a needle fluidly coupled to the dispensing chamber;
  a power source for providing current to the dispensing chamber housing;
  a controller for controlling the power source; and
  a housing at least partially enclosing the dispensing chamber housing, the power source and the controller;
  wherein the controller directs a first current to the dispensing chamber housing to heat the substance contained in the dispensing chamber and a second current to the dispensing chamber housing to alter the shape of the dispensing chamber housing to deliver the substance.

2. The system of claim 1 wherein the device further comprises:
  a thermal sensor located near the dispensing chamber housing, the thermal sensor for measuring a temperature.

3. The device of claim 2 further comprising:
  an interface connecting the thermal sensor to the controller.

4. The device of claim 2 wherein the controller uses the measured temperature to control the first current directed to the dispensing chamber housing.

5. The device of claim 2 wherein the controller uses the measured temperature to control the second current directed to the dispensing chamber housing.

6. The device of claim 1 wherein the controller controls the second current to control an amount of the substance that is delivered.

7. The device of claim 1 wherein the controller controls the second current to control a rate at which the substance is delivered.

8. The device of claim 1 wherein the power source is a rechargeable battery.

9. The device of claim 1 wherein the substance is a drug for treating a condition of the eye.

10. The device of claim 1 wherein the device further comprises:
  an indicator located on the housing, the indicator for providing information about a status of substance delivery.

* * * * *